(12) United States Patent
Hernandez

(10) Patent No.: US 10,188,380 B2
(45) Date of Patent: Jan. 29, 2019

(54) SUTURE ANCHOR SYSTEM WITH COMPRESSIBLE DISTAL TIP

(71) Applicant: DePuy Mitek, LLC, Raynham, MA (US)

(72) Inventor: Joseph Hernandez, Sandwich, MA (US)

(73) Assignee: DePuy Mitek, LLC, Raynham, MA (US)

( * ) Notice: Subject to any disclaimer, the term of this patent is extended or adjusted under 35 U.S.C. 154(b) by 243 days.

(21) Appl. No.: 15/006,653

(22) Filed: Jan. 26, 2016

(65) Prior Publication Data

US 2016/0135802 A1    May 19, 2016

Related U.S. Application Data

(62) Division of application No. 13/278,731, filed on Oct. 21, 2011, now Pat. No. 9,277,911.

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01); *A61B 2017/0414* (2013.01); *A61B 2017/0427* (2013.01); *A61B 2017/0445* (2013.01)

(58) Field of Classification Search
CPC ........ A61B 17/0401; A61B 2017/0409; A61B 2017/0414; A61B 2017/0427; A61B 2017/044; A61B 2017/0445; A61B 2017/0438
See application file for complete search history.

(56) References Cited

U.S. PATENT DOCUMENTS

| | | | |
|---|---|---|---|
| 5,312,438 A | 5/1994 | Johnson | |
| 5,356,413 A | 10/1994 | Martins et al. | |
| 5,383,905 A | 1/1995 | Golds et al. | |
| 5,486,197 A | 1/1996 | Le et al. | |
| 5,522,844 A * | 6/1996 | Johnson | A61B 17/0401 411/447 |
| 5,702,397 A * | 12/1997 | Goble | A61B 17/0401 606/232 |
| 5,733,307 A | 3/1998 | Dinsdale | |
| 6,355,066 B1 | 3/2002 | Kim | |
| 6,436,124 B1 | 8/2002 | Anderson et al. | |
| 6,508,830 B2 | 1/2003 | Steiner | |
| 6,656,183 B2 | 12/2003 | Colleran et al. | |
| 7,309,337 B2 | 12/2007 | Colleran et al. | |

(Continued)

*Primary Examiner* — Jocelin Tanner

(57) ABSTRACT

Methods and devices for fixation of soft tissue to bone are provided. In one embodiment, a suture anchor is provided having an elongate cylindrical body with proximal and distal ends and an inner lumen extending therethrough. The elongate body can be configured so that upon partial insertion into a bone hole, it is securely anchored within the bone hole and a suture extending through the inner lumen is freely slidable. It can also configured so that, upon further insertion into the bone hole, at least a portion of the elongate body compresses to lock the suture within the inner lumen such that the suture is prevented from sliding. In another embodiment, a suture anchor is provided having arms that have an open position for receiving a suture therebetween, and a closed position in which the suture is retained but allowed to slide freely.

4 Claims, 11 Drawing Sheets

(56) References Cited

U.S. PATENT DOCUMENTS

| | | |
|---|---|---|
| 9,023,082 B2 | 5/2015 | Wolf |
| 2002/0161401 A1 | 10/2002 | Steiner |
| 2004/0111117 A1 | 6/2004 | Colleran et al. |
| 2006/0106423 A1 | 5/2006 | Weisel et al. |
| 2006/0253119 A1 | 11/2006 | Berberich et al. |
| 2007/0167950 A1 | 7/2007 | Tauro et al. |
| 2007/0173845 A1* | 7/2007 | Kim .................. A61B 17/0401 606/232 |
| 2009/0076544 A1* | 3/2009 | DiMatteo ........... A61B 17/0401 606/232 |
| 2009/0088798 A1* | 4/2009 | Snyder ............... A61B 17/0401 606/232 |
| 2009/0287246 A1* | 11/2009 | Cauldwell .......... A61B 17/0401 606/232 |
| 2010/0016892 A1 | 1/2010 | Kaiser et al. |
| 2013/0103080 A1 | 4/2013 | Hernandez |
| 2013/0103081 A1 | 4/2013 | Wolf |

* cited by examiner

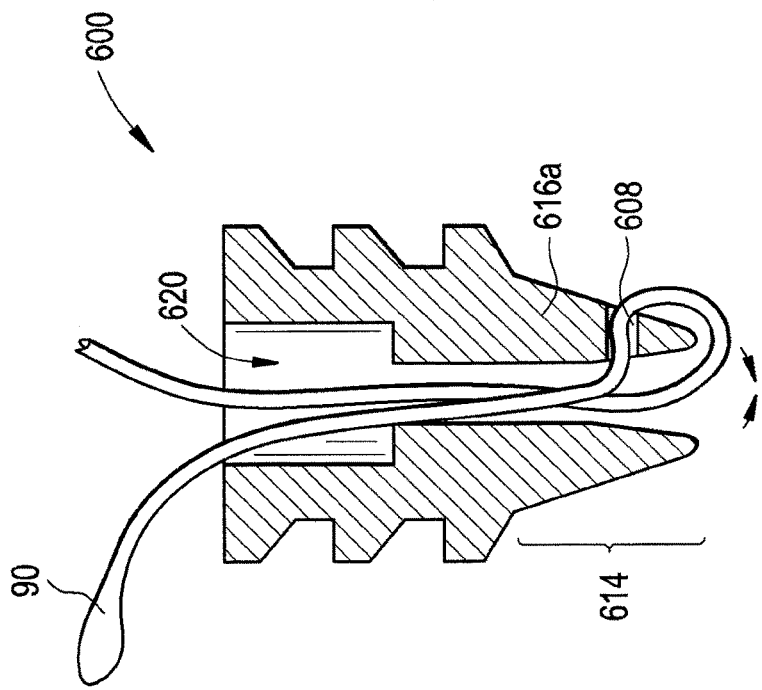
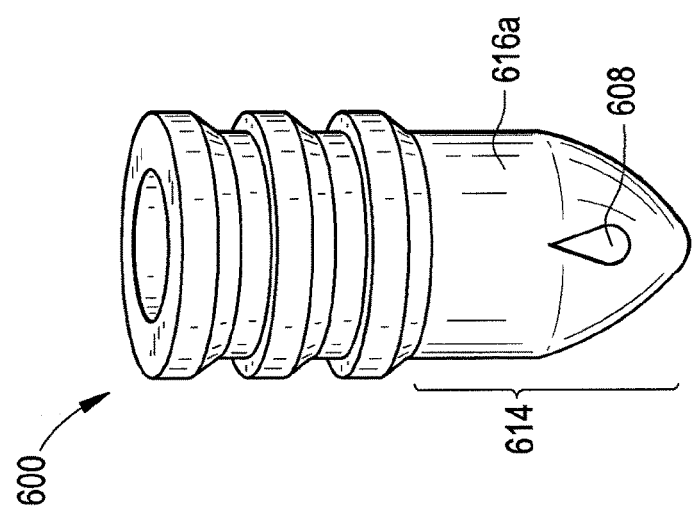

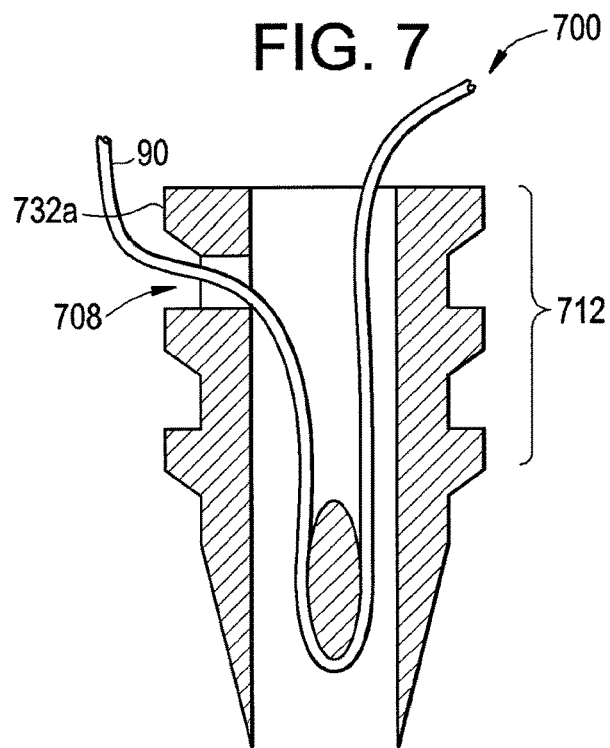
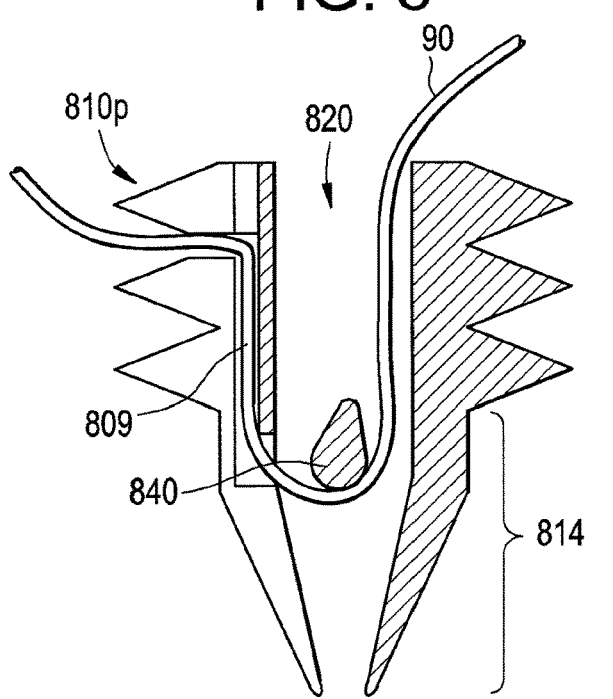

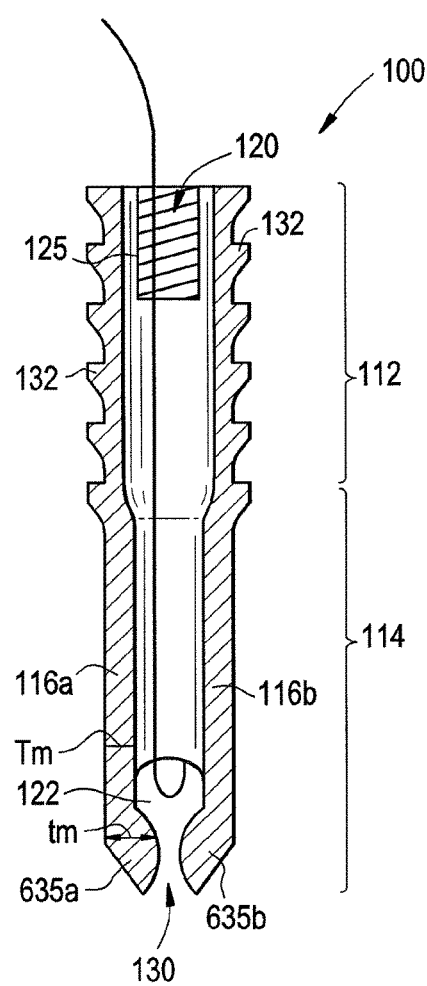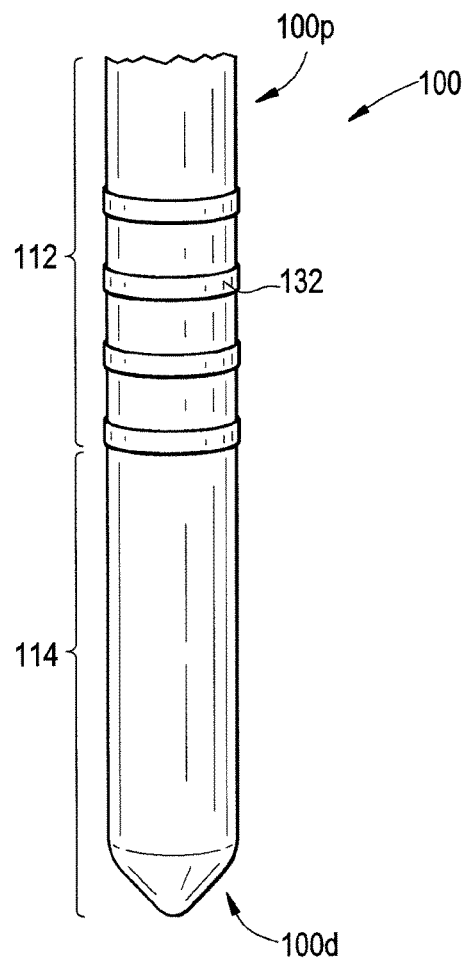

SUTURE ANCHOR SYSTEM WITH COMPRESSIBLE DISTAL TIP

CROSS REFERENCE TO RELATED APPLICATION

The present application is a divisional of U.S. patent application Ser. No. 13/278,731, filed Oct. 21, 2011, and entitled "SUTURE ANCHOR SYSTEM WITH COMPRESSIBLE DISTAL TIP," which is hereby incorporated by reference in its entirety.

FIELD OF THE INVENTION

The present invention relates generally to medical devices and procedures, and more particularly to systems and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently available devices include screws, staples, suture anchors, and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment and a suture anchor is deployed in the hole using an appropriate installation tool. This effectively locks the suture to the bone, with the free end(s) of the suture extending out of the bone. The free ends of the suture are passed through or around the soft tissue and are used to tie the soft tissue securely to the bone.

There remains a need for improved methods and devices for attaching soft tissue to bone.

SUMMARY OF THE INVENTION

The present invention generally provides methods and devices for anchoring soft tissue to bone. In one embodiment, methods and devices are providing having independent mechanisms for fixation of a suture anchor in bone and for fixation of a tension applied to a suture extending between the suture anchor and the tissue being secured. By separating these mechanisms, the present invention allows for less dependence on the interface between the anchor and the bone and greater control over suture tensioning. In an exemplary embodiment, the suture anchor is partially inserted and fixed in the bone prior to tensioning the suture. This can provide a better perspective of the finished state of the repair tension and provide the ability to add or release tension even after fixation of the suture anchor.

In one embodiment, a suture anchor is provided having an elongate substantially cylindrical body having a proximal portion with at least one bone-engaging surface feature formed on an external surface thereof, a flexible distal portion, and an inner lumen extending through the proximal and distal portions. The elongate body can be configured such that, upon insertion of the distal portion into a bone hole and engagement of at least one of the at least one bone-engaging surface features with the bone hole, a suture extending through the inner lumen and coupled to the distal portion is freely slidable. The elongate body can further be configured such that, upon further insertion into the bone hole, the distal portion of the elongate body compresses radially inward to lock the suture within the inner lumen such that the suture is prevented from sliding.

In one embodiment, when the distal portion of the elongate body compresses radially inward, an inner diameter of the proximal portion of the elongate body remains constant and an inner diameter of the distal portion of the elongate body decreases to lock the suture within the inner lumen. An outer diameter of the distal portion of the elongate body can decrease in a distal direction. The distal portion of the elongate body can include, for example, first and second opposed arms having planar inner surfaces that move toward one another when the first and second opposed arms are compressed radially inward.

The elongate body can have a variety of configurations. For example, the at least one bone-engaging surface feature comprises a plurality of circumferential ribs formed on the proximal portion of the elongate body. The elongate body can also have a bore extending through a sidewall thereof and in communication with the inner lumen. In other aspects, the inner lumen can include a suture-engaging member having at least a portion that extends substantially transverse to an axis of the inner lumen, the suture-engaging member being configured to receive a suture there around. The suture-engaging member can have a bore formed therethrough such that a suture can pass through the suture-engaging member. In an exemplary embodiment, the suture-engaging member is U-shaped, and the suture-engaging member extends substantially parallel to opposed planar inner surfaces of the distal portion of the elongate body.

In another embodiment, a suture anchor is provided having an elongate body having proximal and distal ends and an inner lumen extending therethrough. The elongate body can have a drive feature on the proximal end thereof for mating with a driver, at least one bone-engaging surface feature formed on an external surface thereof and configured to engage bone, and a flexible distal tip portion configured to be compressed when advanced into a bone hole to engage a suture extending therethrough. The flexible distal tip portion can have various configurations, and in one aspect the tip has opposed planar inner surfaces configured to engage a suture therebetween when the flexible distal tip portion is compressed. The tip portion can taper radially inward such that an outer diameter decreases in a distal direction. In other aspects, the inner lumen can include a suture-engaging member extending substantially transverse to an axis of the inner lumen. The suture-engaging member can optionally have a lumen extending therethrough such that the suture can pass through the suture-engaging member.

In other aspects, a method for anchoring tissue to bone is provided and includes advancing a bone anchor partially into a bone hole such that the anchor engages the bone and is secured within the bone hole. The bone anchor can have a suture extending through an inner lumen of the bone anchor and coupled to a distal portion of the bone anchor. With the bone anchor partially advanced into the bone hole, the suture can be tensioned to tension tissue coupled to the suture. After tensioning, the bone anchor can be further advanced into the bone hole to cause the distal portion of the bone anchor to compress radially inward and lock the suture therein. In one embodiment, at least one bone engaging surface feature on a proximal portion of the bone anchor engages bone when the bone anchor is partially advanced into the bone hole. In another embodiment, the suture can be threaded through the inner lumen of the bone anchor and through a bore in a sidewall of the bone anchor, or the suture can be threaded around a suture-engaging member extending across the inner lumen of the bone anchor.

In another embodiment, a suture anchor is provided having an elongate body with proximal and distal ends and an inner lumen extending therethrough. The elongate body can have a drive feature on the proximal end thereof for mating with a driver. The elongate body can also have a slot in the distal end defining first and second offset tips that are spaced a distance apart from one another to allow a suture to be received therebetween. The first offset tip can have a first planar surface that is configured to be in sliding contact with a first planar surface of the second offset tip upon compression of the distal end. When the distal tip is compressed and the planar surfaces of the first and second offset tips are in contact with one another, the offset tips can define an eyelet that is configured to retain a suture therein while allowing free sliding movement of the suture relative to the eyelet.

The elongate body can have a number of configurations. For example, in one embodiment, the elongate body can have at least bone-engaging surface feature formed on at least a proximal portion thereof. In another embodiment, an external surface of each of the first and second offset tips can be free of surface features. In one embodiment, the elongate body can include opposed substantially planar outer surfaces formed along a proximal portion thereof.

In another embodiment, the first offset tip can have a second planar surface that extends transverse to the first planar surface of the first offset tip, and the second offset tip can have a second planar surface that extends transverse to the first planar surface of the second offset tip. The first and second planar surfaces of each of the first and second offset tips can be connected by a third substantially cylindrical surface. In other aspects, the first and second offset tips each can have a distal portion with a substantially triangular cross-sectional shape. The first and second offset tips can be positioned on opposed sides of a longitudinal axis of the inner lumen when the elongate body is not compressed. The first and second offset tips can each have a distal portion with a width that is greater than a width of a proximal portion of the offset tip.

In another embodiment, a suture anchor is provided having an elongate body with first and second substantially cylindrical outer surfaces on opposed sides thereof, and first and second substantially planar surfaces on opposed sides thereof and extending between the first and second substantially cylindrical outer surfaces. The anchor can also have first and second arms extending distally from a distal end of the elongate body, the first and second arms being movable between a first position in which the first and second arms are spaced a distance apart from one another to define a slot therebetween for receiving a suture, and a second position in which a planar surface on each of the first and second arms are in sliding contact with one another to form an enclosed eyelet between the first and second arms for capturing a suture therebetween.

The first and second arms can have a number of configurations. In one embodiment, the first and second arms can each have a substantially triangular cross-sectional shape. The first and second arms can be positioned on opposed sides of a longitudinal axis of the elongate body when they are in the first position, and they can intersect the longitudinal axis of the elongate body when they are in the second position. In other aspects, the first and second arms can each have a proximal portion with a maximum width that is less than a maximum width of a distal portion of the first and second arms. The first and second arms can each include a protrusion formed on a distal end thereof, each protrusion having the planar surfaced formed thereon.

In one embodiment, the planar surface on each arm can comprise a first planar surface, and each arm can include a second planar surface that extends in a plane that is transverse to a plane containing the first planar surface. The first and second planar surfaces on each of the first and second arms can be connected by a third substantially cylindrical surface. The planes containing the first and second planar surfaces can extend in a direction substantially parallel to a longitudinal axis of an inner lumen extending through the elongate body. In other aspects, the substantially cylindrical outer surfaces of the elongate body can have threads formed thereon for engaging bone. In other aspects, the substantially cylindrical outer surfaces of the elongate body can have a plurality of ridges formed thereon for engaging bone.

BRIEF DESCRIPTION OF THE DRAWINGS

The invention will be more fully understood from the following detailed description taken in conjunction with the accompanying drawings, in which:

FIG. 6A is a side view of a suture anchor according to another embodiment, having a bore formed through an arm of a flexible distal tip;

FIG. 6B is a cross-sectional view of the suture anchor of FIG. 6A;

FIG. 7 is a cross-sectional view of another embodiment of a suture anchor having a bore extending through a sidewall of a proximal portion of the suture anchor;

FIG. 8 is a cross-sectional view of another embodiment of a suture anchor having an elongate lumen extending through a sidewall of the suture anchor;

FIG. 10A is a cross-sectional view of another embodiment of a suture anchor;

FIG. 10B is a side view of the suture anchor of FIG. 9A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for anchoring suture to bone. In one embodiment, a suture anchor is provided and it includes an elongate substantially cylindrical body having proximal and distal ends and an inner lumen extending therethrough. The elongate body has a proximal portion that is configured to engage bone, and a distal portion that is configured to receive a suture therein, and to flex and engage the suture. In use, upon partial insertion into a bone hole, the proximal portion can engage bone to securely anchor the suture anchor within the bone hole, and the distal portion allows a suture extending through the inner lumen to be freely slidable. Upon further insertion of the elongate body into the bone hole, the distal tip portion can compress radially inward to lock the suture within the inner lumen such that the suture is prevented from sliding. Such a configuration is particularly advantageous as it allows a tension of the suture to be adjusted after the bone anchor is engaged in the bone hole. Once the tension is properly adjusted, the tension can be locked by simply further driving the anchor into the bone hole.

Figure 1A:
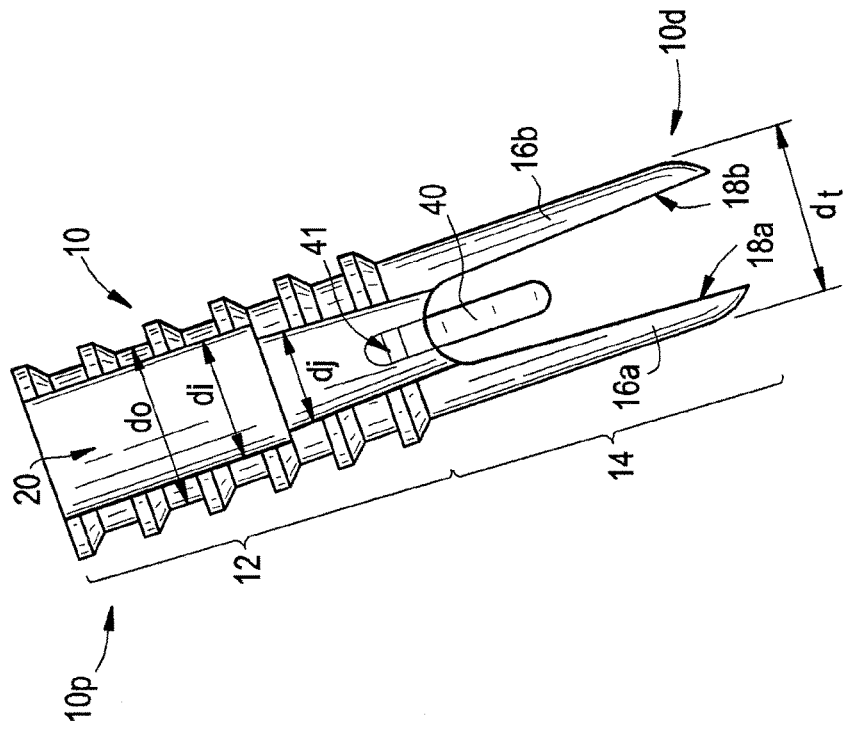
FIG. 1A is a perspective view of one embodiment of a suture anchor.
Figure 1B:
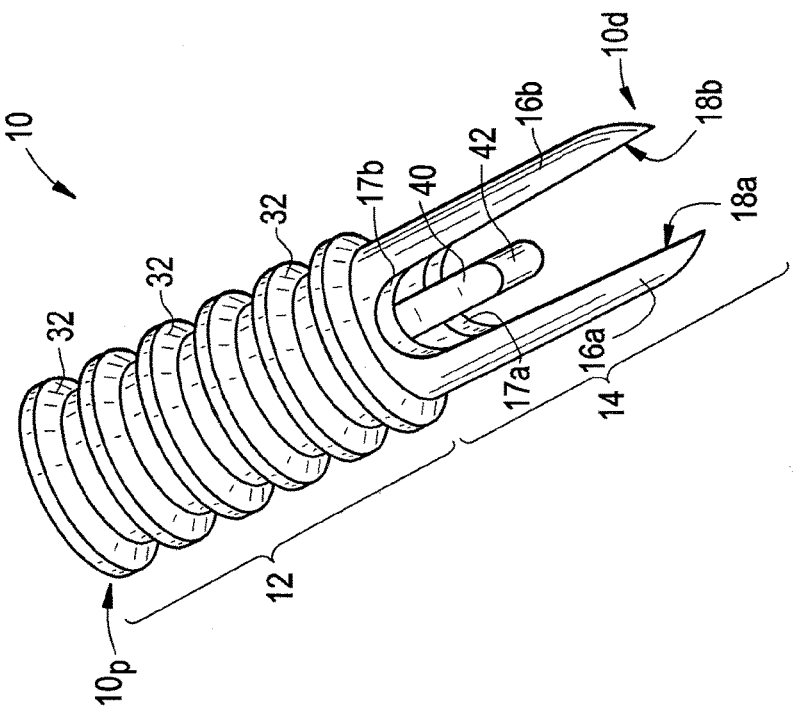
FIG. 1B is a cross-sectional view of the suture anchor of FIG. 1A.

FIGS. 1A-1B illustrate one embodiment of a suture anchor 10 having an elongate body that is configured to be partially inserted into a bone hole and to allow free slidable movement of a suture extending therethrough, and to be fully inserted into a bone hole to engage and lock the suture therein. In general, the suture anchor 10 has an elongate body with proximal and distal ends 10p, 10d and an inner lumen 20 extending therethrough. A proximal portion 12 of the elongate body can have a generally cylindrical shape and can be configured to engage bone to anchor the suture anchor 10 within a bone hole. A distal portion 14 of the elongate body can be flexible or compressible to allow a suture extending therethrough to slide freely when the distal portion 14 is resting and not compressed, and to be secured or locked in a fixed position when the distal portion 14 is compressed.

The proximal portion 12 of the elongate body can have a variety of configurations. In an exemplary embodiment, as indicated above, the proximal portion 12 is configured to engage bone. As such, the proximal portion 12 is preferably substantially rigid, and can have a generally cylindrical shape to allow the proximal portion 12 to fit securely within a cylindrical bone hole. While not shown, the proximal portion 12 can, however have one or more planar sidewalls, grooves, or other surface variations.

In order to facilitate engagement of bone, the proximal portion 12 can include one or more bone-engaging surface features formed on an external surface thereof for securely anchoring the suture anchor 10 within a bone hole, even when the suture anchor is only partially inserted. As shown in FIGS. 1A-1B, the proximal portion 12 includes a plurality of flanges 32 circumferentially formed around the external surface of the anchor, and spaced axially along the anchor. While the bone-engaging surface features in the illustrated embodiment are in the form of a plurality of circumferential axially-spaced flanges, a person skilled in the art will understand that one or more of various surface-engaging features can be used, such as teeth, ridges, threads, barbs, protrusions, etc. The surface-engaging features 32 can be located on the entire external surface of the suture anchor 10, or on any portion thereof. In an exemplary embodiment, as shown, the flanges 32 or other surface-engaging features are formed around only the proximal portion 12 and extend from the proximal end 10p and terminate just proximal to the distal tip portion 14, which is free from surface-engaging features. Such a configuration allows the distally-positioned flanges 32 to engage bone when the suture anchor 10 is only partially inserted into a bone hole, while the distal tip portion 14 remains free to flex. The particular location along the elongate body at which the surface-engaging features 32 terminate can vary depending on the particular configuration of the suture anchor 10.

The inner lumen 20 that extends through the elongate body can also have a variety of configurations, but the inner lumen 20 is preferably configured to receive one or more sutures therein. The inner lumen can also be configured to receive a driver for driving the suture anchor 10 into the bone. As shown in FIG. 1B, the inner lumen 20 has a first diameter $d_i$ at a proximal portion thereof that is greater than a diameter $d_j$ at a distal portion thereof, such that the proximal portion of the inner lumen 20 can receive a driver. Various techniques can be used to facilitate engagement between the inner lumen and a driver mechanism. For example, the inner lumen, or at least the proximal portion thereof, can have an asymmetrical shape that complements a corresponding asymmetrical shape of a driver. The asymmetrical portion preferably extends along a substantial length of the inner lumen so as to maximize surface contact between a driver and the suture anchor. While not shown, the proximal portion of the inner lumen 20 can have various shapes and sizes, such as hexagonal, to allow it to be keyed to a driver. A person skilled in the art will appreciate that, while a headless suture anchor is shown, the proximal end 10p of the suture anchor 10 can alternatively have a head formed thereon and configured to mate with a driver.

Figure 1C:
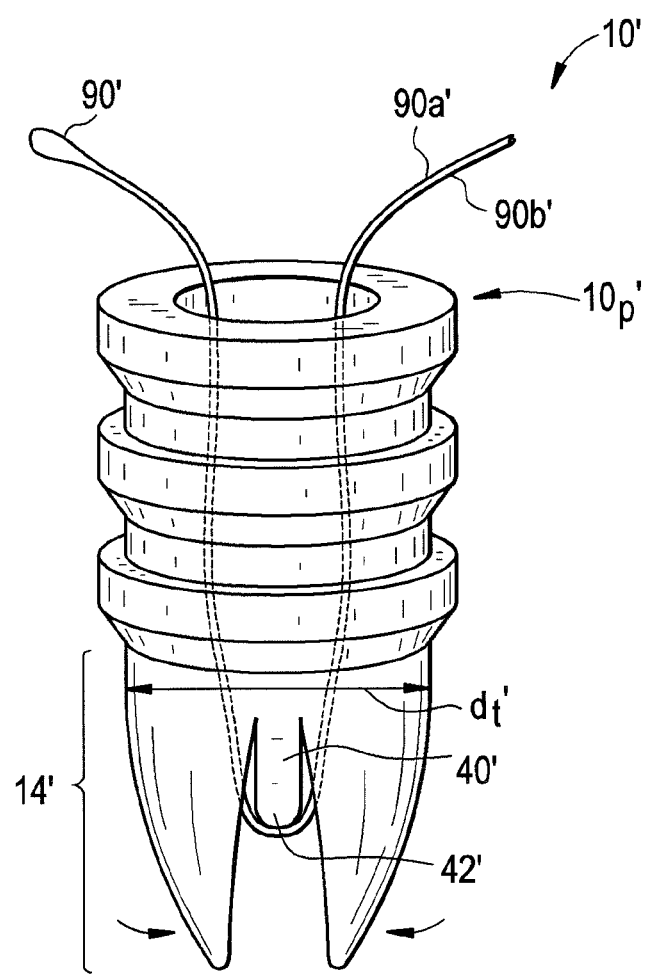
FIG. 1C is a partially transparent view of the suture anchor of FIG. 1A having a suture extending therethrough.

As indicated above, the suture anchor 10 has a flexible distal tip portion 14 that is configured to compress upon insertion into a bone hole and to engage a suture extending therethrough. While the tip 14 can have a variety of configurations, in an exemplary embodiment the tip portion 14 has a generally cylindrical outer surface. The outer diameter $d_t$ of the tip portion 14 can remain substantially constant along the entire length thereof, and the diameter $d_t$ can be greater than, less than, or equal to a minor diameter $d_o$ of the proximal portion 12 of the suture anchor 10. Alternatively, FIG. 1C illustrates an embodiment of a suture anchor 10' having a similar configuration to suture anchor 10 (like reference numerals are used to refer to like parts), however the tip portion 14' is tapered distally such that an outer diameter $d_t'$ of the tip portion 14' at the proximal end is greater than an outer diameter of the tip portion 14 at the distal end. In an exemplary embodiment, the diameter of the distal tip portion is configured to aid in compression of the distal tip portion upon insertion into a bone hole, and more particularly into a bone hole having a tapered terminal end or a bone hole having a reduced-diameter region, as will be discussed in more detail below.

To allow compression of the distal tip portion 14, the tip portion 14 can include one or more longitudinally-oriented slots formed therein. The flexibility of the tip can vary depending on the number and configuration of the slots, and a person skilled in the art will appreciate that the tip can be configured to have a desired flexibility. While the size, quantity, position of slots can vary, in the illustrated embodiment the distal tip portion 14 has first and second axially opposed U-shaped slots 17a, 17b formed therein that define first and second opposed arms 16a, 16b. The length of the slots 17a, 17b can be configured to provide a desired flexibility of the opposed arms 16a, 16b. By way of non-limiting example, the slots 17a, 17b can extend along about 20% to 50% of the entire length of the suture anchor 10. For example, the slots 17a, 17b can have a length in the range of about 3 mm to 7 mm. The distal tip portion 14 can thus likewise have a length that is about 20% to 50% of the entire length of the suture anchor 10. In an exemplary embodiment, the distal tip portion 14 has a length in the range of about 2 mm to 5 mm. Longer distal tips may provide better fixation with a reduced risk of breakage.

The shape of each arm 16a, 16b can also vary. In an exemplary embodiment, the outer surface of each arm 16a, 16b is generally cylindrical. The inner surface of the arms 16a, 16, however, can vary to facilitate engagement of a suture extending therethrough. FIGS. 1A-1C illustrates arms 16a, 16b having planar inner surfaces 18a, 18b, respectively. Such a configuration can allow the surfaces 18a, 18b to engage a suture therebetween when moved together during compression of the tip portion 14. As further shown in FIGS. 1A-1C, the distal-most end of the arms 16a, 16b, and thus of the tip portion 14, can be blunt or rounded to facilitate introduction into a bone hole.

The suture anchor 10 can also include one or more suture-engaging or receiving members formed therein and configured to receive a suture. The suture-engaging member can have a variety of configurations, and it can be integrally formed with the suture anchor, i.e., the suture anchor and suture-engaging member can be molded as a single unit or formed from a single piece of material, or the suture-engaging member can be fixedly or removably mated to the suture anchor. The suture-engaging member can also be rotatably disposed within the inner lumen.

In one embodiment, the suture-engaging member can be in the form of a post, pin, rod, or arm having at least a portion that extends across the lumen between opposed inner surfaces of the body. The particular shape and location of the suture-engaging member can vary, but it is preferably configured to receive a suture therearound to retain the suture within the lumen 20, and more preferably within a distal portion of the lumen 20, e.g., between the opposed arms 16a, 16b. As illustrated in FIGS. 1A-1C, the suture-engaging member 40 is in the form of a U-shaped member having opposed terminal ends (only one end 41 is shown in FIG. 1B) that are coupled to opposed inner surfaces of the body at a location just proximal to the slots 17a, 17b formed in the distal tip portion 14. The terminal ends of the suture-engaging member 40 are preferably axially aligned with the slots 17a, 17b such that the suture-engaging member 40 extends substantially parallel to the inner planar surfaces 18a, 18b of each arm 16a, 16b. A mid-portion 42 of the U-shaped suture-engaging member 40 can extend transversely across the inner lumen 20 in a direction substantially perpendicular to the longitudinal axis of the inner lumen 20. It will be understood by a person skilled in the art that the angular orientation of the suture-engaging member can vary relative to a longitudinal axis of the inner lumen 20. In use, as shown in FIG. 1C, a suture 90' can be wrapped around the mid-portion 42' of the suture-engaging member 40', with terminal ends 90a', 90b' of the suture 90' extending out of the proximal end 10p' of the suture anchor 10'.

The particular location of the suture-engaging member 40, and in particular the mid-portion 42 of the suture-engaging member 40, within the inner lumen 20 can also vary. In the embodiment of FIGS. 1A-1C, the mid-portion 42 of the suture-engaging member 40 is positioned distal of the terminal ends (only end 41 is shown) of the suture-engaging member and distal to a proximal-most end of each slot 17a, 17b, such that the mid-portion 42 is located between the flexible arms 16a, 16b of the distal tip portion 14. Such a configuration will allow a suture 90 extending around the mid-portion 42 to be engaged between the arms 16a, 16b and the mid-portion 42 of the suture-engaging member 40.

FIGS. 2A-8 illustrate additional embodiments of suture anchors having configurations similar to suture anchor 10, with various modifications Like reference numerals are used to refer to like parts, with a different prefix used for each embodiment. The suture anchors illustrated in FIGS. 2A-8 can thus have all of the features discussed above with respect to FIGS. 1A-1C. Moreover, a person skilled in the art will appreciate that a suture anchor according to the present invention can include any combination of features disclosed herein, including the features discussed and illustrated with respect to FIGS. 2A-8.

Figure 2B:
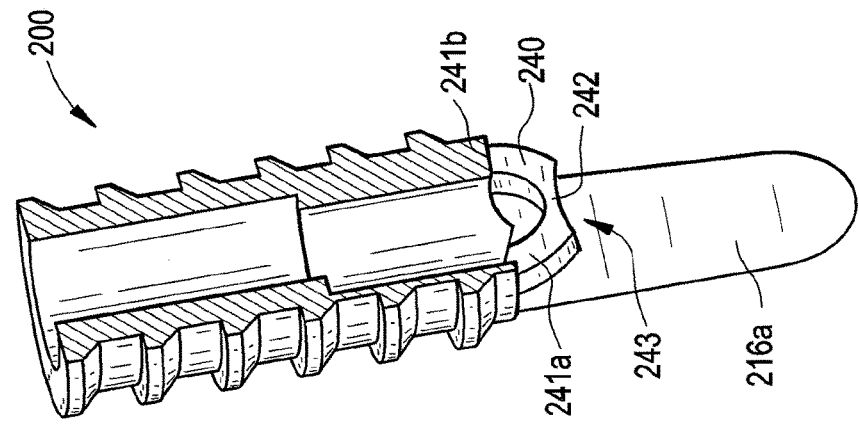
FIG. 2B is a is a cross-sectional view of the suture anchor of FIG. 2A.
Figure 2A:
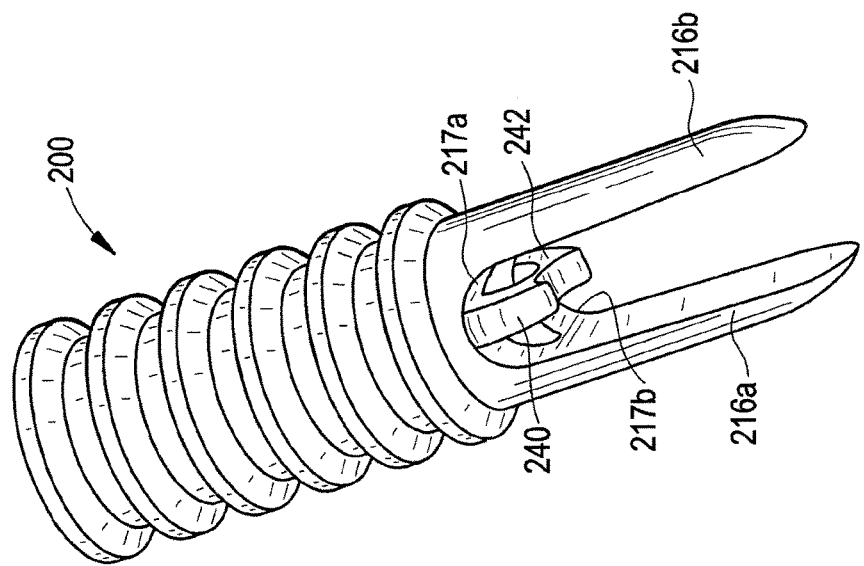
FIG. 2A is a perspective view of another embodiment of a suture anchor similar to the suture anchor of FIG. 1A, but having a suture-engaging member positioned more proximal.

FIGS. 2A-2B illustrates another embodiment of a suture anchor 200 in which the suture-engaging member 240 is located more proximal than the position of the suture-engaging member 40 of FIGS. 1A-1B. In particular, in this embodiment the mid-portion 242 of the suture-engaging member 240 is positioned closer to the proximal ends of the arms 216a, 216b, but yet still located distal of a proximal-most end of each slot 217a, 217b extending between the arms 216a, 216b. The opposed terminal ends 241a, 241b of the suture-engaging member 240 can be coupled to the proximal-most end of each slot 217a, 217b.

The suture-engaging member 240 can include various features formed thereon to facilitate positioning of a suture extending there around. As shown in FIGS. 2A-2B, a distal-facing surface of the mid-portion 242 (i.e., the portion extending generally transverse to the axis of the lumen) of the suture-engaging member 240 includes a groove or concavity 243 formed therein and configured to seat a suture.

Figure 3:
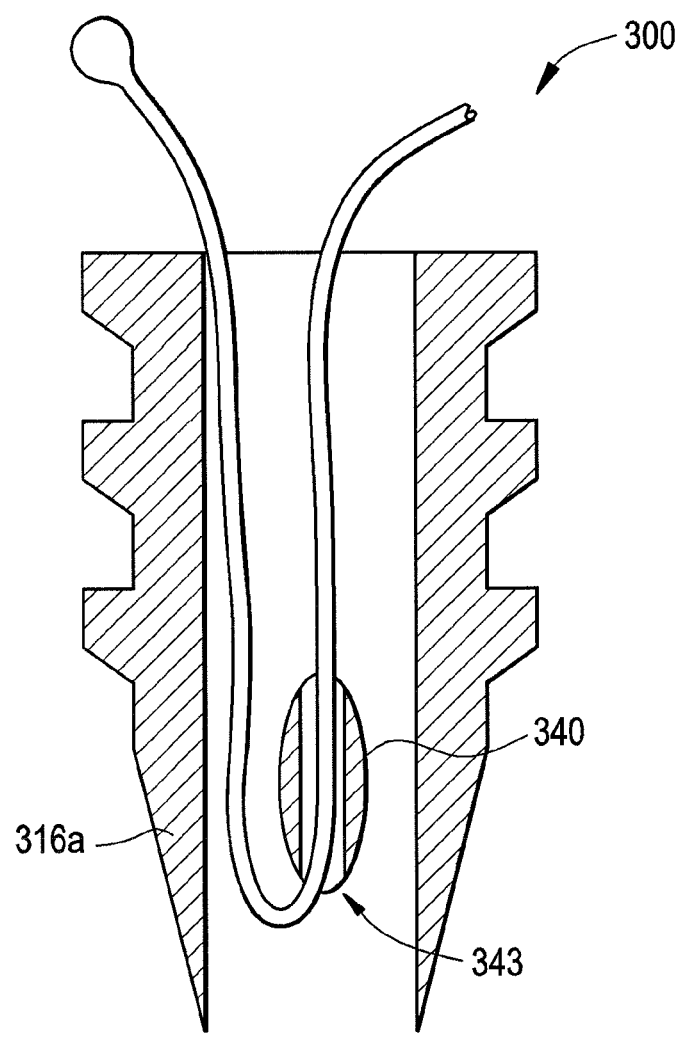
FIG. 3 is a cross-sectional view of another embodiment of a suture anchor similar to FIG. 1A, but having a bore formed through the suture-engaging member.

In another embodiment of a suture anchor 300, shown in FIG. 3, the suture engaging member 340 can have a bore 343 formed therethrough such that one or more sutures can pass through the bore 343 and around one side of the suture-engaging member 340. Such a configuration will allow a suture to be engaged between one arm 316a and the suture-engaging member 340.

Figure 4:
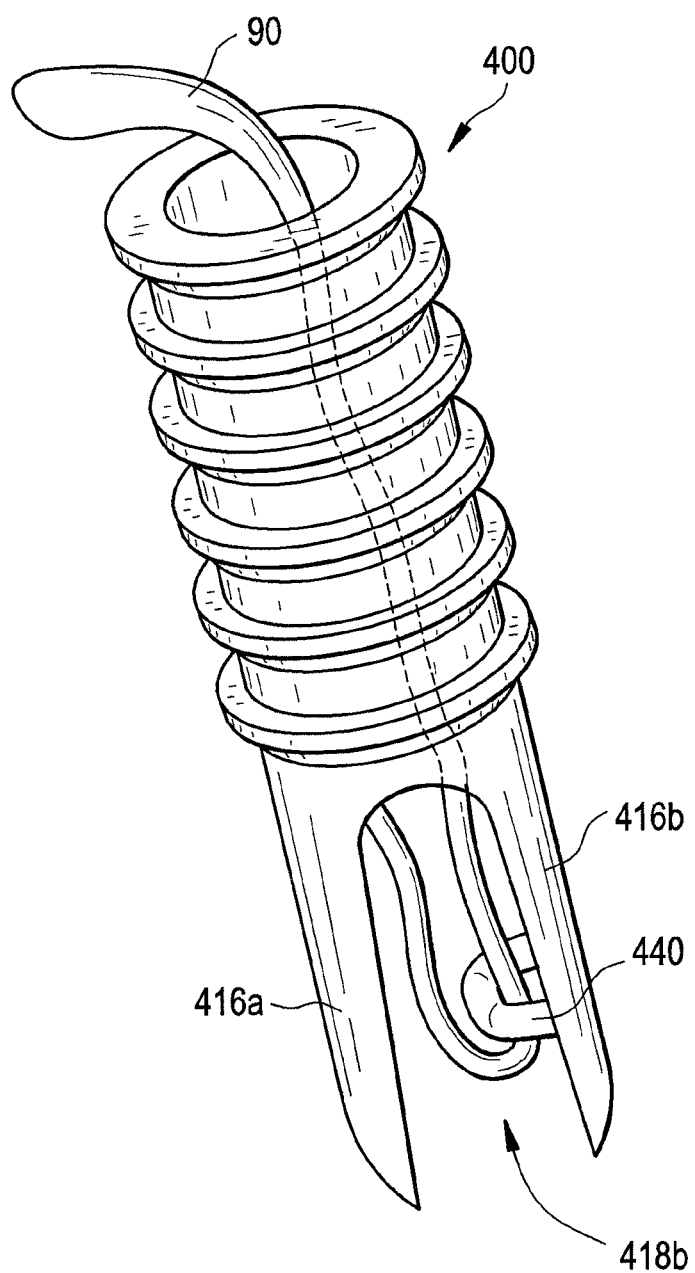
FIG. 4 is a perspective view of yet another embodiment of a suture anchor having a suture-engaging member formed on an arm of a flexible distal tip

In another embodiment of a suture anchor 400, as shown in FIG. 4, the suture-engaging member 440 can be coupled to one arm, e.g., arm 416b, of the distal tip portion 414. In this embodiment, the suture-engaging member 440 is U-shaped with opposed terminal ends that are mated adjacent to opposed lateral sides of the arm 416b. The suture-engaging member 440 thus extends in a plane that is perpendicular to the inner planar surface 418b of the arm 416b. Similar to anchor 300, the suture 90 will be engaged between one arm, e.g., arm 416a and the suture-engaging member 440.

Figure 5:
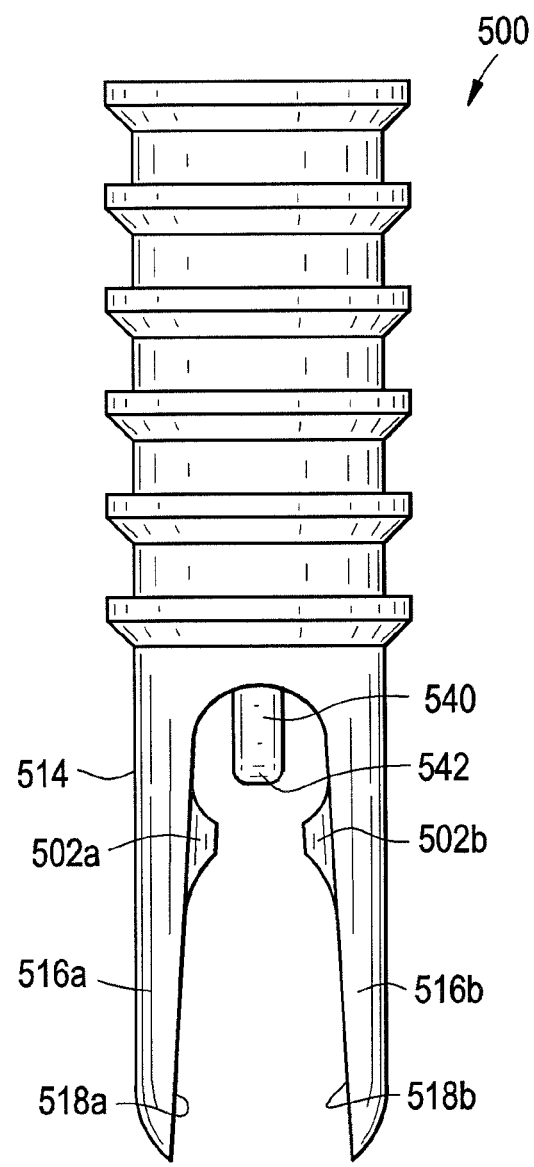
FIG. 5 is a side view of another embodiment suture anchor similar to FIG. 1A, but having surface features for facilitating engagement of a suture.

The arms of the flexible distal tip portion can also include other features to facilitate engagement of a suture. FIG. 5, for example, illustrates another embodiment of a suture anchor 500 that is similar to anchor 10, but that includes a surface protrusion 502a, 502b formed on the inner planar surface 518a, 518b of each arm 516a, 516b of the distal tip portion 514. The surface protrusions 502a, 502b can have various shapes and sizes and can be located anywhere along the arms 516a, 516b. As shown in FIG. 5, the protrusions 502a, 502b are directly opposite one another and are positioned just distal to the mid-portion 542 (e.g., transversely extending portion) of the suture-engaging member 540. Each protrusion 502a, 502b extends in a direction generally parallel to a direction of the mid-portion 542 of the suture-engaging member 540. The positioning of the protrusions 502a, 502b can facilitate further engagement of a suture extending around the suture-engaging member 540. For example, when the arms 516a, 516b are compressed inward, the protrusions 502a, 502b can tilt proximally and engage a suture against the suture-engaging member 540. A person skilled in the art will appreciate that the inner planar surface 518a, 518b can include other features, such as teeth, indentations, or a textured surface to facilitate engagement of a suture.

In other aspects, the suture anchor can include one or more bores, lumens, or pathways formed through a sidewall thereof for receiving the suture. For example, FIGS. 6A-6B illustrate one embodiment of a suture anchor 600 having a bore 608 extending through one of the arms 616a of the flexible distal tip portion 614. The bore 608 is positioned adjacent to a distal-end of the arm 616a to allow a suture 90 to extend through the lumen 620 of the suture anchor 600, pass through the bore 608, wrap around the distal-most end of the arm 616a, and extend back through the lumen 620, as shown in FIG. 6B. In use, when the arms 616a, 616b are compressed, the suture will be engaged directly between the arms 616a, 616b. In another embodiment shown in FIG. 7, the proximal portion 712 of the suture anchor 700 can have a bore 708 extending through the sidewall thereof to receive at least a portion of the suture 90 therethrough. The bore 708 in this embodiment is located just distal of the proximal-most flange 732a on the suture anchor 700. This will allow the suture 90 to remain freely slidable when the suture anchor 700 is partially inserted into bone, such that the bore 708 will not yet be disposed within the bone hole. Once the anchor 700 is fully inserted into a bone hole, the portion of the suture 90 extending out of the bore 708 and along the outside of the suture anchor 700 will be engaged between the suture anchor 700 and the bone hole, thus providing an additional means for fixation. A person skilled in the art will appreciate that the bore 708 can extend at any angle and can be positioned at various locations. Moreover, rather than a bore 708, the suture anchor can include a lumen. For example, in another embodiment of a suture anchor 800 shown in FIG. 8, an elongate lumen 809 can extend through a sidewall of the suture anchor 800 and can communicate with the inner lumen 820. The lumen 809 can originate at a location within the flexible distal tip portion 814 adjacent to the suture-engaging member 840, and the lumen 809 can exit in a sidewall of the anchor 800 at a location just distal to the proximal end 810p of the anchor 800. Such a configuration can function similar to suture anchor 700 described above with respect to FIG. 7. Alternatively, the lumen 809 can exit at the proximal-most surface of the suture anchor 800.

The suture anchors disclosed herein can be formed from various biocompatible materials including, by way of non-limiting example, metals, such as surgical grade titanium, and polymers, such as poly-ether-ether-ketone (PEEK), polylactic acid, polyglycolic acid, and combinations thereof. Exemplary materials include, by way of non-limiting example, a composite of tricalcium phosphate and poly (lactic-co-glycolic acid), such as Biocryl Rapide™ available from DePuy Mitek, Inc. The properties of the material can depend on the particular configuration of the suture anchor. For example, the inner lumen of the suture anchor can have a length that maximizes the torque strength of the suture anchor as well as the amount of surface contact between a driver and the suture anchor, thus allowing weaker materials, such as bioabsorbable and/or osteoconductive materials to be used. A cannulated suture anchor is also particularly advantageous as it allows materials, such as bone-growth promoting materials, sealants, adhesives, etc., to be introduced therein to facilitate fixation. In one embodiment, the material can have physical properties that are sufficient to allow a driver to be inserted into the inner lumen of the suture anchor and to be used to drive the suture anchor into bone without damaging the suture anchor. The material can also have physical properties that are sufficient to allow compression of the elongate body of the suture anchor without damaging the suture anchor. In other aspects, the material can allow directional compression, so that although it is compressible in one plane, little to no compression can occur in another plane. A person skilled in the art will appreciate that a variety of other materials, including plastics and metals, can be used to form the suture anchor. Various portions of the suture anchor can also be formed from different materials to provide distinct advantages. For example, the flexible distal tip portion can be formed from either the same or different materials than the remainder of the suture anchor. In particular, the distal tip portion can be made of a material with a greater degree of flexibility or elasticity than the body, or portions thereof, such as the bone-engaging surface members. In other aspects, portions of the suture anchor that engage with the bone hole, such as the bone-engaging surface features formed on the external surface of the proximal portion of the suture anchor, can be made of a rigid, non-flexible material.

The present invention also provides exemplary methods for anchoring tissue to bone. While a method is described in connection with attaching soft tissue to bone, the methods and devices disclosed herein can be used in a variety of medical procedures for anchoring one structure to another.

In general, a bone hole or tunnel is formed in bone of a patient. The diameter of the tunnel is preferably less than a major diameter of the suture anchor, e.g., the thread or flange diameter, and substantially the same as the minor diameter of the suture anchor. The length of the tunnel can be the same as or slightly greater than a length of the suture anchor to allow the suture anchor to be fully disposed thereon, however the length can vary depending on the configuration of the anchor. The hole can extend fully through the cortical bone to allow the suture anchor to be fully engaged through the thickness of the cortical bone. The bone hole can also extend into the cancellous bone depending on the length of the suture anchor. The bone hole can have various shapes depending on the configuration of the suture anchor. In an exemplary embodiment, however, the bone hole is tapered at its distal end to allow the tapered portion of the bone hole to compress the distal tip portion of the suture anchor as it is being driven into the bone hole.

Figure 9B:
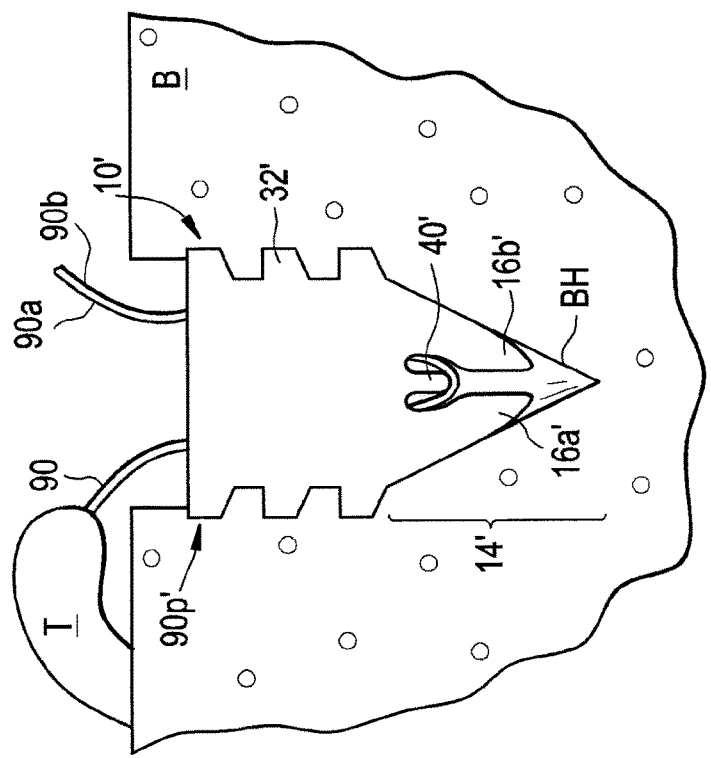
FIG. 9B is a side view of the suture anchor of FIG. 9A shown fully inserted into the bone hole.
Figure 9A:
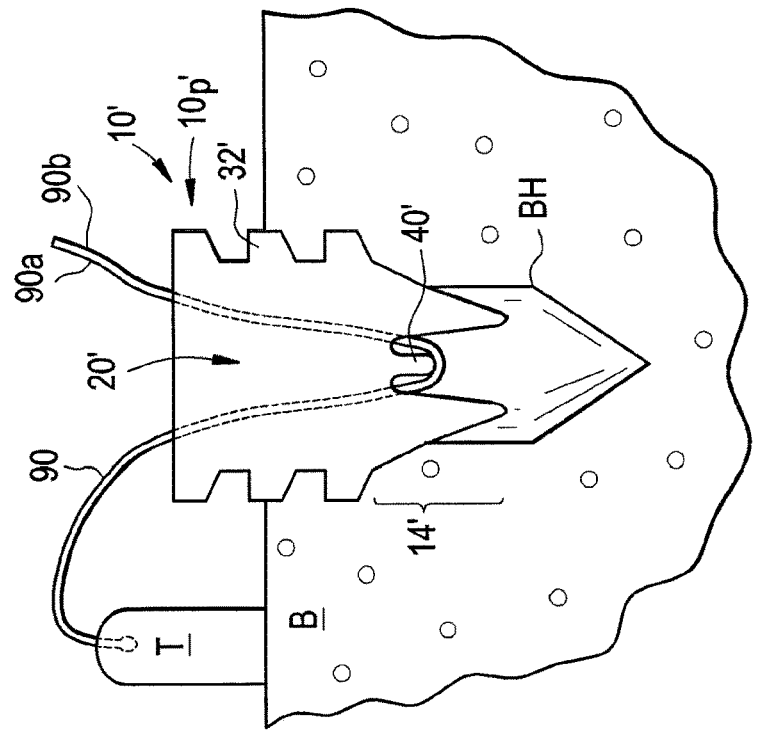
FIG. 9A is a partially transparent side view of the suture anchor of FIG. 1C shown partially inserted into a bone hole.

One or more sutures can be coupled to the suture anchor using various techniques. As described above, the one or more sutures can have a variety of configurations, including being threaded through the inner lumen of the bone anchor, threaded through a bore or lumen in the sidewall of the bone anchor, threaded around a suture-engaging member, threaded through a suture-engaging member, threaded around a flexible arm, or the suture(s) can enter and exit the same end of the anchor, or any combination of these. With reference to FIGS. 9A and 9B, which illustrate suture anchor 10' by way of non-limiting example, in one embodiment the method can include coupling a suture 90 to a suture anchor 10' such that the suture 90 extends around a suture-engaging member 40' formed in the flexible distal tip portion 14' of the suture anchor 10 and trailing ends 90a, 90b of the suture 90 extend through the inner lumen 20' and out the proximal end 10p' of the suture anchor 10'.

Once the suture 90 is coupled to the anchor 10', the distal tip of a driver (not shown) can be inserted into the lumen 20' in the suture anchor 10'. The trailing ends of the suture(s) can extend externally along the driver or they can extend through an inner lumen of the driver. The driver can then be used to insert the suture anchor 10' into the bone hole BH. For example, where the suture anchor 10' includes flanges 32' formed thereon, the driver can be impacted to drive the suture anchor 10' into the bone hole. The flanges 32' will engage the bone hole BH thereby preventing removal of the suture anchor 10'. In other embodiments, the driver can be used to tap or rotate the bone anchor into the bone hole, and an interference fit, compression fit, and/or surface features, such as ribs, barbs, or protrusions, formed on the suture anchor can be used to retain the suture anchor within the bone hole. In an exemplary embodiment, the suture anchor 10' is inserted such that the entire distal tip portion 14' is disposed within the bone hole BH and at least a portion of the bone-engaging surface features, e.g., one, two, or three flanges 32', are disposed within the bone hole BH and in engagement with bone B, as shown in FIG. 9A. In an exemplary embodiment, at least about 40% to 80% of the entire length of the suture anchor 10' is disposed within the bone hole during "partial" insertion. The anchor 10' is preferably inserted only to a depth in which the suture anchor 10' is secured within the bone hole and will not pull out, and the distal tip portion 14' is not compressed so that the suture remains freely slidable to allow a tension on the suture to be adjusted.

Once the suture anchor 10' is partially anchored within the bone hole, the suture 90 can be appropriately tensioned to apply the proper amount of tension to the attached tissue T. The trailing ends 90a, 90b of the suture 90 can be used to anchor the soft tissue T to the bone B. For example, one or both trailing ends 90a, 90b of the suture 90 can be attached to a needle to allow the needle to be used to thread the suture through tissue to be anchor to the bone. The suture(s) can be threaded through tissue either prior to or after insertion of the suture anchor into bone. Once the soft tissue is approximated toward the bone and the desired tension is achieved, the driver can be used to further advance the suture anchor 10' into the bone hole BH. As shown in FIG. 9B, the shape of the bone hole BH will cause the flexible distal tip portion 14' to compress radially inward to lock the suture 90 within the inner lumen 20' such that the suture 90 is prevented from sliding. As shown, in this embodiment the suture 90 is in direct engagement between the arms 16a', 16b' and the suture-engaging member 40'.

Figure 10C:
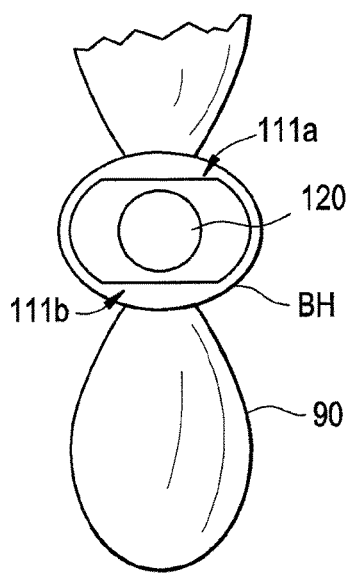
FIG. 10C is a top view of the suture anchor of FIG. 9A inserted in a bone hole.

FIGS. 10A-10D illustrate another embodiment of a suture anchor 100 having a compressible distal tip portion that has an open configuration for receiving a suture therein, and that upon insertion into a bone hole, closes to retain a freely slidable suture in an eyelet therein. The suture anchor 100 can have an elongate body with proximal and distal ends 100p, 100d. A proximal portion 112 can be configured to engage bone, and a distal portion 114 can have opposed arms 116a, 116b can be configured to move together to form an eyelet 122 effective to retain a suture, such that the suture retained therein remains freely slidable. The suture anchor 100 can also have an inner lumen 120 extending therethrough, as shown in FIGS. 10A and 10C.

The proximal portion 112 of the suture anchor 110 can have a variety of shapes and size, and in general can have the same configuration and features as previously discussed above with respect to the suture anchors of FIGS. 1A-8, including a drive feature 125 (FIG. 10A) formed in a proximal portion of the lumen 120 for mating with a driver, and bone-engaging surface features 132 located on an external surface thereof. As further illustrated in FIG. 10C, the proximal portion 112 of the suture anchor 110 can also optionally include opposed planar outer surfaces 111a, 111b to create a gap when inserted in a bone hole BH for receiving a suture 90, as shown. This can allow a suture positioned between the planar surface 111a, 111b and the bone hole BH to freely slide to adjust tension.

The flexible distal arms 116a, 116b can also be similar to the previous embodiment in that the arms 116a, 116b can extend distally from the proximal portion 112 and are configured to move together upon compression in a bone hole. In this embodiment, however, the distal arms 116a, 116b can be configured to move between an open position shown in FIG. 10A, in which a suture can be passed through an opening 130 formed between the distal ends of the arms 116a, 116b, and a closed position, in which the arms 116a, 116b form an eyelet 123, shown in FIG. 10E, to prevent removal of the suture while still allowing free movement of the suture.

Figure 10D:
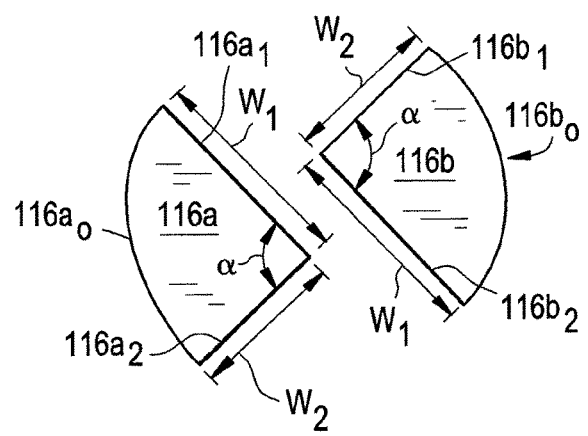
FIG. 10D is a bottom view of offset tips of the suture anchor of FIG. 9A.
Figure 10E:
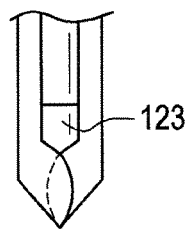
FIG. 10E is an enlarged view of the distal portion of the suture anchor of FIG. 10A shown inserted into a bone hole.

While the arms 116a, 116b can have various shapes and sizes, as shown in FIG. 10D, the arms 116a, 116b can each be generally elongate with an enlarged distal tip 635a, 635b having a somewhat triangular shape, with one side being rounded. In particular, the outer surface $116a_o$, $116b_o$ of each tip 635a, 635b can be generally cylindrical, and each tip 635a, 635b can include first and second planar inner surfaces $116a_1$, $116a_2$, $116b_1$, $116b_2$. The first planar inner surface $116a_1$, $116b_1$ on each tip 635a, 635b can extend at an angle α relative to the second planar inner surface $116a_2$, $116b_2$ of each tip 635a, 635b. The angle α can vary, but in an exemplary embodiment the angle is in the range of about 45 degrees to 135 degrees, and more preferably is about 90 degrees. The width of each planar surface can also vary, but in an exemplary embodiment one of the first and second planar surfaces on each tip 635a, 635b has a width that is different than the other one of the first and second planar surfaces on that tip 635a, 635b. As shown in FIG. 10D, the first planar surface 116$a_1$, 116$b_1$ on each tip 635a, 635b has a width $w_1$ that is greater than a width $w_2$ of the second planar surface 116$a_2$, 116$b_2$. As a result, each tip 635a, 635b will be offset from one another. In particular, the first planar surface 116$a_1$, 116$b_1$ of each 635a, 635b will be in facing relationship with one another, but the surfaces 116$a_i$, 116$b_1$ will be offset. The first and second offset tips 635a, 635b can be positioned in various ways, such as on opposed sides of a longitudinal axis of the suture anchor 100 when the suture anchor 100 is not compressed and is in a resting position. The offset tips 635a, 635b can be spaced a distance apart from one another to allow a suture 90 to be received in the slot or gap 122 defined therebetween. When the arms 116a, 116b are compressed together upon insertion into a bone hole, the first planar surface 116$a_1$, 116$b_1$ of each tip 635a, 635b will come into sliding contact with one another to thereby close the gap 122 and form an enclosed eyelet 123, as shown in FIG. 10E. A suture disposed within the eyelet 123, however, will still be freely slidable.

The eyelet 123 can result from the arms 116a, 116b increasing in width or thickness at the tips 635a, 635b. In particular, the first and second offset tips 635a, 635b can each have a maximum thickness $t_m$ that is greater than a maximum thickness $T_m$ of a proximal portion of the arms 116a, 116b. In other words, the tips 635a, 635b can be in the form of protrusions formed on the inner surface of each arm 116a, 116b.

The suture anchor can have various sizes, and by way of non-limiting example the anchor can have a diameter of about 3.5 mm and a length of about 13 mm. The drill used to create the bone hole can vary based on various factors, such as the bone and the particular suture anchor being used, but in one embodiment the drill can have a diameter of about 2.9 mm and a length of approximately 9 mm long.

The suture anchor can be formed from various biocompatible materials including, by way of non-limiting example, metals, such as surgical grade titanium, and polymers, such as poly-ether-ether-ketone (PEEK), polylactic acid, polyglycolic acid, and combinations thereof. Exemplary materials include, by way of non-limiting example, a composite of tricalcium phosphate and poly(lactic-co-glycolic acid), such as Biocryl Rapide™ available from DePuy Mitek, Inc. Various portions of the suture anchor 610 can also be formed from different materials to provide distinct advantages. For example, portions of the suture anchor 610 that engage with the bone hole, such as the bone-engaging elements 332, may be made of a material that is resilient to frictional forces, whereas the portions of the flexible distal tip 635 that are compressible or flexible may be constructed from more compressible or flexible materials.

In use, a suture 90 can be passed through the open distal tips 635a, 635b, and the anchor 100 can be inserted into a bone hole. The bone hole will cause compression of the distal tips 635a, 635b toward one another, thereby moving the first planar surfaces 116$a_1$, 116$b_1$ into sliding contact with one another. As a result, the tips 635a, 635b will close forming an enclosed eyelet 123, which traps the suture 90 therein. The tension of the suture 90 can be adjusted by sliding the suture along the anchor. A knot or other fixation techniques can be used to fix the suture and thereby anchor soft tissue coupled to the suture to bone.

A person skilled in the art will appreciate that the suture anchors disclosed herein can be configured for use with one or more sutures. The particular quantity of sutures used with a suture anchor can depend on the size of the suture anchor and the driver, and in particular on the diameter of the inner lumen of the suture anchor.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for anchoring tissue to bone, comprising:
   advancing a bone anchor partially into a bone hole such that the anchor engages the bone and is secured within the bone hole, the bone anchor having a suture extending through an inner lumen of the bone anchor and coupled to a distal portion of the bone anchor;
   tensioning the suture, with the bone anchor partially advanced into the bone hole, to tension tissue coupled to the suture; and
   after tensioning, further advancing the bone anchor into the bone hole to cause the distal portion of the bone anchor to compress radially inward and lock the suture therein.

2. The method of claim 1, wherein at least one bone engaging surface feature on a proximal portion of the bone anchor engages bone when the bone anchor is partially advanced into the bone hole.

3. The method of claim 1, wherein the suture is threaded through the inner lumen of the bone anchor and through a bore in a sidewall of the bone anchor.

4. The method of claim 1, wherein the suture is threaded around a suture-engaging member extending across the inner lumen of the bone anchor.

* * * * *